United States Patent
Sowards-Emmerd et al.

(10) Patent No.: US 9,466,133 B2
(45) Date of Patent: Oct. 11, 2016

(54) DOSE-OPTIMIZED PROTOCOL FOR AC AND LOCALIZATION ON HYBRID SCANNERS

(75) Inventors: David Sowards-Emmerd, San Jose, CA (US); Joerg Bredno, San Francisco, CA (US); Eberhard Sebastian Hansis, Hamburg (DE); Sven Prevrhal, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 290 days.

(21) Appl. No.: 14/124,289

(22) PCT Filed: May 23, 2012

(86) PCT No.: PCT/IB2012/052581
§ 371 (c)(1),
(2), (4) Date: Dec. 6, 2013

(87) PCT Pub. No.: WO2012/168813
PCT Pub. Date: Dec. 13, 2012

(65) Prior Publication Data
US 2014/0119630 A1 May 1, 2014

Related U.S. Application Data

(60) Provisional application No. 61/495,504, filed on Jun. 10, 2011.

(51) Int. Cl.
| G06T 11/00 | (2006.01) |
| A61B 6/03 | (2006.01) |
| A61B 6/00 | (2006.01) |

(52) U.S. Cl.
CPC ............ *G06T 11/005* (2013.01); *A61B 6/032* (2013.01); *A61B 6/037* (2013.01); *A61B 6/5205* (2013.01); *A61B 6/5217* (2013.01); *A61B 6/5235* (2013.01); *G06T 11/008* (2013.01)

(58) Field of Classification Search
None
See application file for complete search history.

(56) References Cited

U.S. PATENT DOCUMENTS

| 6,740,883 B1 | 5/2004 | Stodilka et al. |
| 2008/0187095 A1* | 8/2008 | Boone .................. A61B 6/0435 378/37 |
| 2011/0058722 A1 | 3/2011 | Hu et al. |

FOREIGN PATENT DOCUMENTS

WO 2010018478 A1 2/2010

OTHER PUBLICATIONS

Elstrom, R. L., et al.; Combined PET and low-dose, noncontrast Ct scanning obviates the need for additional diagnostic contrast-enhanced CT scans in patients undergoing staging or restaging for lymphoma; 2008; Annals of Oncology; 19:1770-1773.
Wechalekar, K., et al.; PET/CT in oncology—a major advance; 2005; Clinical Radiology; 60:1143-1155.

* cited by examiner

*Primary Examiner* — Vu Le
*Assistant Examiner* — Alexander J Lesnick

(57) ABSTRACT

A hybrid imaging system including a first imaging system configured to acquire low resolution anatomical data of a first field of view of an anatomical structure. A second imaging system is configured to acquire functional data of the first field of view of the anatomical structure. A reconstruction processor is configured to reconstruct the functional data based on attenuation data into an attenuation corrected image. In response to the attenuation corrected image showing regions of interest, with the first imaging system or another imaging system acquiring high resolution data of one or more portions of the first field of view containing the regions of interest. The reconstruction processor reconstructs the high resolution anatomical data into one or more high resolution images of the regions of interest.

20 Claims, 3 Drawing Sheets

DOSE-OPTIMIZED PROTOCOL FOR AC AND LOCALIZATION ON HYBRID SCANNERS

CROSS REFERENCE TO RELATED APPLICATIONS

This application is a national filing of PCT application Serial No. PCT/IB2012/052581, filed May 23, 2012, published as WO 2012/168813 A1 on Dec. 13, 2012, which claims the benefit of U.S. provisional application Ser. No. 61/495,504 filed Jun. 10, 2011, which is incorporated herein by reference.

The present application relates to diagnostic imaging systems and methods. It finds particular application in reducing patient dose and accelerating workflow of multi-modality imaging systems combining MRI, CT, and one of PET or SPECT, but may find applicability in other diagnostic or treatment systems.

In multi-modality or hybrid imaging systems, two different sensing modalities, such as nuclear imaging scanners like PET or SPECT coupled with an anatomical imaging scanner such as CT, XCT, MRI, and the like are used to locate or measure different constituents in the object space. For example, the PET and SPECT scanners create functional images indicative of metabolic activity in the body, rather than creating images of surrounding anatomy. CT scanners allow doctors to see internal structures such as bones and tissue within the human body; while MRI scanners visualize soft tissue structures like the brain, spine, vasculature, joints, and the like.

Before a hybrid imaging scanning procedure, a patient receives a dose of a radiopharmaceutical. The pharmaceutical is carried through the blood and concentrates in one or more target organs or regions and emits radiation. During a nuclear scanning procedure, the emitted radiation is detected by the system and reconstructed into an image of the distribution of the radiopharmaceutical in the patient. The image can show the circulatory system and/or the relative absorption of the radiopharmaceutical in various regions or organs. Canerous tumors, for example, absorb significant quantities of glucose containing radiopharmaceuticals. Integration of anatomical data from an anatomical scanning procedure with the metabolic data from the nuclear scanning procedure in a hybrid image gives physicians visual information to determine if disease is present, the location and extent of disease, and track how rapidly it is spreading. Hybrid imaging systems are particularly helpful in difficult-to-treat regions (e.g. head and neck area, mediastinum, postsurgical abdomen) and localization of the treatment area for the patients receiving radiation therapy or chemotherapy.

Anatomical imaging data can also be used for attenuation correction to further enhance nuclear imaging data. Attenuation correction in traditional nuclear imaging systems can involve a transmission scan in which an external radioactive transmission source rotates around a field of view (FOV) and measures the attenuation through the examination region. CT images are also used for attenuation correction.

The hybrid imaging system uses the anatomical data to construct an attenuation map of density differences throughout the body and to correct for absorption of emitted photons. Anatomical based attenuation correction benefits from low statistical noise, high speed acquisition, immunity from injected radioisotope related interference, and the elimination of radioactive transmission source hardware. Typically, the patient is first imaged with a high resolution, high dose CT imaging system before starting the nuclear imaging scanning procedure. In some systems, a high resolution MRI imaging system is used. The anatomical based scans cover the full FOV of the nuclear imaging system. Thus, the current procedure involves scanning the patient at a high dose over a larger extent of the patient as attenuation correction and anatomical data is needed for the entire nuclear medicine acquisition.

For hybrid imaging systems, acquisition time is a market distinguisher. Currently, the typical procedure on a hybrid imaging system is to acquire a full diagnosis high resolution CT image, spanning the full region of the patient to be examined. After the CT image is generated, a nuclear image of the examined region is generated. The CT image is registered to the nuclear image and used for attenuation correction when reconstructing the nuclear image. If the nuclear image shows hot spot, the registered CT image is used to identify the location of the hot spot in the anatomy and the surrounding anatomy. If the nuclear image shows no hot spots or other regions of interest, the CT image is only used for attenuation correction.

The present application provides a new and improved apparatus and method which overcomes the above-referenced problems and others.

In accordance with one aspect, a hybrid imaging system is provided. The hybrid imaging system including a first imaging system configured to acquire low resolution anatomical data of a first field of view of an anatomical structure. A second imaging system is configured to acquire functional data of the first field of view of the anatomical structure. A reconstruction processor is configured to reconstruct the functional data based on attenuation data into an attenuation corrected image. In response to the attenuation corrected image showing regions of interest, with the first imaging system or another imaging system acquiring high resolution data of one or more portions of the first field of view containing the regions of interest. The reconstruction processor reconstructs the high resolution anatomical data into one or more high resolution images of the regions of interest.

In accordance with another aspect, a method is provided. The method including acquiring low resolution anatomical data of a first field of view of an anatomical structure, acquiring functional data of the first field of view of the anatomical structure, reconstructing the functional data using the low resolution data for attenuation correction into an attenuation corrected image, analyzing the attenuation corrected image to identify any regions of interest, acquiring high resolution anatomical data in second fields of view which encompass the regions of interest, the second fields of view being smaller than and confined in the first field of view, and reconstructing the high resolution anatomical data into one or more high resolution images.

In accordance with another aspect, a method is provided. The method includes generating a functional image covering a first field of view of a patient, analyzing the function image for regions of interest including in response to identifying one or more regions of interest, generating one or more high resolution images covering one or more second fields of views, each second field of view encompassing at least one region of interest and being smaller than and contained in the first field of view, and in response to identifying no regions of interest, terminating the method without generating a high resolution image.

One advantage resides in reduced patient dose.

Another advantage resides in improved workflow.

Another advantage resides in greater imaging efficiency and patient throughput

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
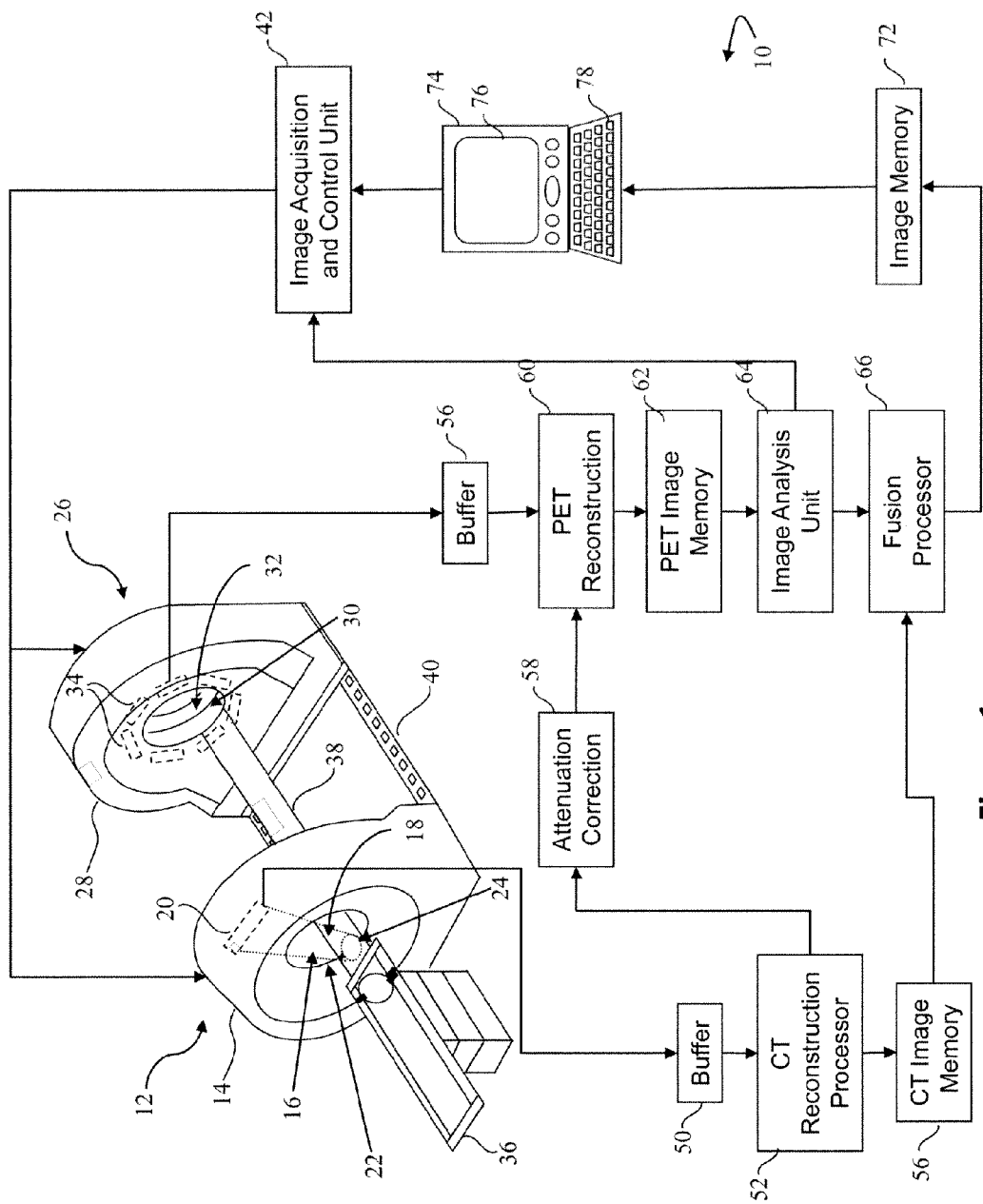
FIG. 1 is a diagrammatic view of combined PET/CT system in accordance with the present application.

FIG. 1 illustrates a hybrid imaging system 10 which implements a workflow that optimizes image quality while decreasing dose to the patient and minimizing scan length and/or duration. The workflow, described in detail below, begins with an attenuation correction (AC) scan using a low-dose computer tomography (CT) or a fast magnetic resonance (MR) imaging procedure and a Single Photon Emission Computed Tomography (SPECT) and/or Positron Emission Tomography (PET) acquisition. Once the Nuclear Medicine (NM) acquisition has completed, a preliminary reconstruction with the attenuation correction data is performed. The attenuation corrected nuclear image is then immediately reviewed to determine if and where detailed anatomical image would be beneficial for diagnosis (bone fracture, lesion/hot spot localization). If a follow-on scan is not required to generate the detailed anatomical image, then the patient only received a low-dose AC scan as opposed to an order of magnitude larger dose associate with a high resolution diagnostic CT scan. If a detailed anatomical image would be advantageous, then a high resolution scan is generated of the sub regions identified in the nuclear scan. Optionally, a low resolution AC image of the whole region can be combined with the high resolution CT images of the sub regions to create a hybrid image with high resolution in the sub regions of interest and lower resolution in the other portion of the examined region. Additionally, several scan parameters including exposure, positioning, collimation, filter, MR protocol etc., can be optimized to further reduce the patient dose while providing excellent image quality for regions of interest.

With reference to FIG. 1, a multimodality imaging system employs at least two different imaging modalities. In the illustrative examples set forth herein, the multi-modality imaging facility employs computed tomography (CT) and positron emission tomography (PET) imaging modalities using a hybrid PET/CT imaging system 10 that includes a CT scanner 12, housed within a first gantry 14. A bore 16 defines a first examination region 18 of the CT scanner 12. An array of radiation detectors 20 is disposed on a rotating gantry 22 configured to receive transmission radiation from an x-ray source 24 disposed opposite the detectors 20 on the rotating gantry 22. The hybrid PET/CT imaging system 10 also includes a PET scanner 26 housed within a second gantry 28 which defines a patient receiving bore 30. A ring of radiation detectors 34 are arranged around the bore 30 to define a second or PET examination region 32.

In the illustrated embodiment. The two gantries 14, 28 are adjacent to one another and share a common patient support 36 that translates along a longitudinal axis between the two examination regions 18, 32 along a patient support track or path 38. A motor or other drive mechanism (not shown) provides the longitudinal movement and vertical adjustments of the support in the examination regions 18, 32. In the illustrated embodiment, the PET gantry 28 translates along a gantry track 40 to reduce the transit time and distance between imaging systems 12, 26. A closed arrangement between gantries reduces the likelihood of patient movement and mis-registration errors stemming from increased scan times.

A different type of hybrid PET/CT imaging system, or another type of hybrid imaging system such as a hybrid magnetic resonance MR/PET imaging system or so forth can be provided in addition to or in place of the illustrated hybrid PET/CT imaging system 10. Moreover, multimodality imaging can instead or additionally be provided by one or more standalone imaging systems, such as a standalone low dose CT scanner, C-arm x-ray scanner, a standalone high dose CT scanner, a standalone PET scanner, a standalone MR scanner, a standalone gamma camera configured for SPECT imaging, or so forth. Still further, in some embodiments a single imaging instrument may be configured to provide multimodality imaging. For example, it is contemplated for the multimodality imaging system to include PET and MR systems in a common gantry, PET and a low dose radiation source in a single gantry, PET and CT in a common gantry, and the like.

With continuing reference to FIG. 1, the patient support 36 positions the patient or subject to be imaged into the first examination region 18 and an imaging acquisition and control unit 42 controls an x-ray tube and cooperating x-ray detector array (components disposed in the CT scanner 12 and not visible in FIG. 1) to generate and acquire low dose CT projection data. For example, while a conventional CT scan typically has a dose of around 30 mGy, a low dose CT scan would reduce the dose by 85%, to around 6 mGy. The acquired low dose T projection data is temporarily stored in a data buffer 50 and reconstructed by a CT reconstruction processor 52 to generate one or more low dose CT images that are stored in a CT images memory 56. The CT reconstruction processor 52 also generates information indicative of the radiation attenuation of the patient or subject being examined in the first examination space 18. The attenuation information is generally expressed in Hounsfield Units (HU). An attenuation map is generated from the attenuation information by an attenuation correction unit 58 which is used by a PET reconstruction processor 60 to generate an attenuation corrected PET image representation. Information from the attenuation map is used to correct for errors resulting from non-uniform radiation attenuation characteristics of the patient or subject being examined (e.g., the presence of bones in a human patient).

In similar fashion, the patient support 36 positions the patient or subject to be imaged into the second examination region 32 and the imaging acquisition and control unit 42 operates PET radiation detectors 34 to acquire PET line-of-response data (optionally including time-of-flight localization). The PET line-of-response data is temporarily stored in a data buffer 56 and reconstructed by a PET reconstruction processor 60 to generate one or more PET images that are stored in a PET image memory 62. The attenuation map generated by the attenuation correction unit 58 is used by a PET image reconstruction processor 60 to generate an attenuation corrected PET image representation from the PET data. In the case of PET imaging, a suitable positron-emitting radiopharmaceutical is administered to the subject prior to the PET data acquisition. The emitted positrons undergo positron/electron annihilation with each such annihilation event generating 511 keV gamma rays travelling in opposite directions, thus defining a line-of-response.

In another embodiment, the PET data is collected before the CT data. In a further variation, the PET data is direst reconstructed without attenuation correction. If the image without the attenuation correction is adequate to determined that no high resolution scan is needed, the low dose scan for generating the attenuation map can also be omitted.

The one or more PET images are analyzed to determine if and where detailed anatomical information is beneficial for the diagnosis of the patient. Specifically, the PET images are analyzed by an image analysis unit 64 to determine if a region of interest is within the field of view. Specifically, the image analysis unit 64 identifies regions of potential interest, e.g. regions which include a potential hot spot or object of interest within the field of view of the PET image. Regions of interest include objects of interest based on identification criteria, a particular object of interest such as, for example, a left ventricle of the heart, a tumor, or the like. If it is determined that a region of interest is not within the field of view of the PET image, the image analysis unit 64 determines a follow up localization or diagnosis CT scan is not required, the patient will then only receive a low dose CT scan as opposed to an order of magnitude larger dose localization or diagnosis scan. If a region of interest is within the field of view of the PET image, the image analysis unit 64 analyzes the quality of the low dose CT scan to determine if a follow up localization or diagnosis CT scan is required. For example, if it is determined that the low dose CT images are of high enough quality to be used for diagnosis, the patient will only be required to receive a low dose CT scan as opposed to a localization or diagnosis scan. If it is determined that the low dose CT image are not of high enough quality for diagnosis and a more detailed scan is desired, a follow up localization or diagnosis scan is performed. If a follow up localization or diagnosis scan is to be performed, the image analysis unit 64 utilizes the volume/registration information of the low dose CT scan for precisely targeting the localization or diagnosis scan. Specifically, the registration between the attenuation map and PET image scan provides for precise positioning to allow for a small field-of-view localization and diagnosis scans. For example, if the field of view of the low dose CT scan includes a region of interest, the image analysis unit 64 will calculate a second smaller field of view which includes the region of interest but not the complete examination region to reduce patient dose. It is also contemplated that the image acquisition and control unit 42 optimize several scan parameters including exposure, positioning, collimation, filter, MR protocol, and the like to further reduce the patient dose while providing excellent image quality for regions of interest.

If it is determined that detailed anatomical information is beneficial for the diagnosis, the imaging acquisition and control unit 42 controls the patient support 36 to position the patient or subject into the first examination region 18 and controls the x-ray tube and cooperating x-ray detector array (components disposed in the CT scanner 12 and not visible in FIG. 1) to generate and acquire localization or diagnostic CT projection data. To reduce patient dose, the localization or diagnosis scan is limited to the field-of-view calculated by the image analysis unit 64. The localization or diagnostic CT projection data typically has a dose of around 30 mGy for the full examination region. By scanning only sub volumes, e.g. slabs, encompassing each region of interest, the dose of the high resolution scan is reduced. The acquired localization or diagnostic CR projection data is temporarily stored in a data buffer 50 and reconstructed by a CT reconstruction processor 52 to generate one or more localization or diagnostic CT images that are stored in a CT images memory 56.

A fusion processor 66 aligns, registers, or fuses the attenuation correction PET image representation and the localization or diagnostic high resolution CT image representation(s) and, in some embodiments, the low resolution x-ray image to generate a fused image. The individual images and the fused image are displayed on a display 76 e.g. of a computer 74. The attenuation corrected PET image representation, fused images, and others, are displayed on the display 76. The display also includes an input device 78 which a clinician can use for controlling the imaging system to select scanning sequences and protocols, fused image combinations, and the like. The graphic user interface also displays pre-corrected and corrected images concurrently for verification and/or further manual correction.

The imaging acquisition and control unit 42 are suitably embodied by a digital processor or controller, or by a combination of digital processors or controllers, operating in combination with suitable electronics, power supplies, and so forth configured to operate the x-ray tube and radiation detector arrays, to operate a rotational mechanism that revolves the x-ray tube around the subject within the CT scanner 12, and so forth. The image analysis unit 64 is suitably embodied by a digital processor or controller optionally in combination with dedicated imaging acquisition and control hardware embodied, for example, as application-specific integrated circuitry (ASIC) hardware. The reconstruction processors 52, 60 are suitably embodied by a digital processor or controller, or by a combination of digital processors or controllers, optionally in combination with dedicated reconstruction pipeline hardware embodied, for example, as application-specific integrated circuitry (ASIC) hardware. A user interface, such as the illustrated computer 74, is provided to enable a radiologist or other user to configure, initiate, and monitor CT and PET imaging sessions, and to enable the radiologist or other user to view the resulting CT and/or PET images. The illustrated computer 74 includes a display 76, which may be embodied as a cathode-ray tube (CRT) display, a liquid crystal device (LCD) display, a plasma display, an organic light emitting device (OLED) display, or so forth. The computer 74 also includes a keyboard 78; however, additional or other input devices (not shown) may also be included such as a trackpad, a trackball, a touch-sensitive matrix coincident with the display 76 to define a touch-sensitive screen, or so forth. In some embodiments, some user interfacing functionality may be integrated with the CT scanner 12 and/or the PET scanner 26 as a built-in LCD display, built-in keypad, or so forth.

Figure 2:
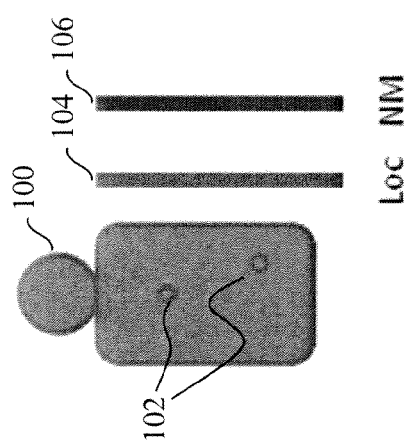
FIG. 2 is a diagrammatic illustration of a traditional hybrid imaging scan procedure in accordance with the present application.

With reference to FIG. 2, a traditional hybrid imaging scan procedure is illustrated. A patient 100 includes one or more regions of interest 102, e.g. regions which include a hot spot or object of interest. In the traditional hybrid imaging scan procedure, a full field of view localization or diagnosis scan 104 is performed with an anatomical imaging scanner to collected attenuation and anatomical data of the patient 100 and the one or more regions of interest 102. After the localization or diagnosis scan 104 is performed, a nuclear imaging scanner performs a full field of view nuclear imaging scan 106 to acquire functional data of the patient 100 and the one or more regions of interest 102. In the traditional hybrid imaging scan, the patient is imaged with a high resolution, high dose anatomical imaging scan ner and attenuation and anatomical data is acquired for the entire field of view.

Figure 3:
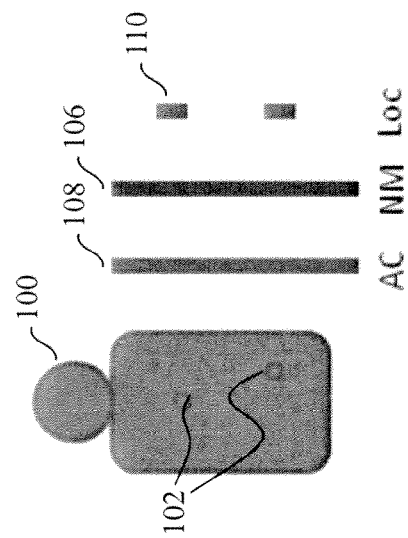
FIG. 3 is a diagrammatic illustration of a low dose hybrid imaging scan procedure in accordance with the present application.

With reference to FIG. 3, a low dose hybrid imaging scan procedure is illustrated. The patient 100 includes the one or more regions of interest 102. In the low dose hybrid imaging scan procedure, a full field of view low dose scan 108 is performed with an anatomical imaging scanner to collected attenuation data of the patient 100 including the one or more regions of interest 102. After the low scan 106 is performed, a nuclear imaging scanner performs a full field of view nuclear imaging scan 106 to acquire functional data of the patient 100 including the one or more regions of interest 102. The attenuation data is used to generate the attenuation map which is used to generate the attenuation corrected functional image. The functional image is immediately reviewed to determine if and where anatomical data is beneficial for diagnosis (bone fracture, lesion/hot spot localization). If a localization or diagnosis scan is not required, then the patient only received a low-dose scan as opposed to an order of magnitude larger dose localization or diagnostic scan. If a localization or diagnosis scan is desired, the registration between the attenuation and functional data provides the precise positioning to allow for a small field of view localization or diagnosis scan which images only sub volumes or slabs 110. A small field of view localization or diagnosis scan 110 is performed with an anatomical imaging scanner to collected anatomical data or portion(s) of the patient 100 that contain the one or more regions of interest 102.

Figure 4:
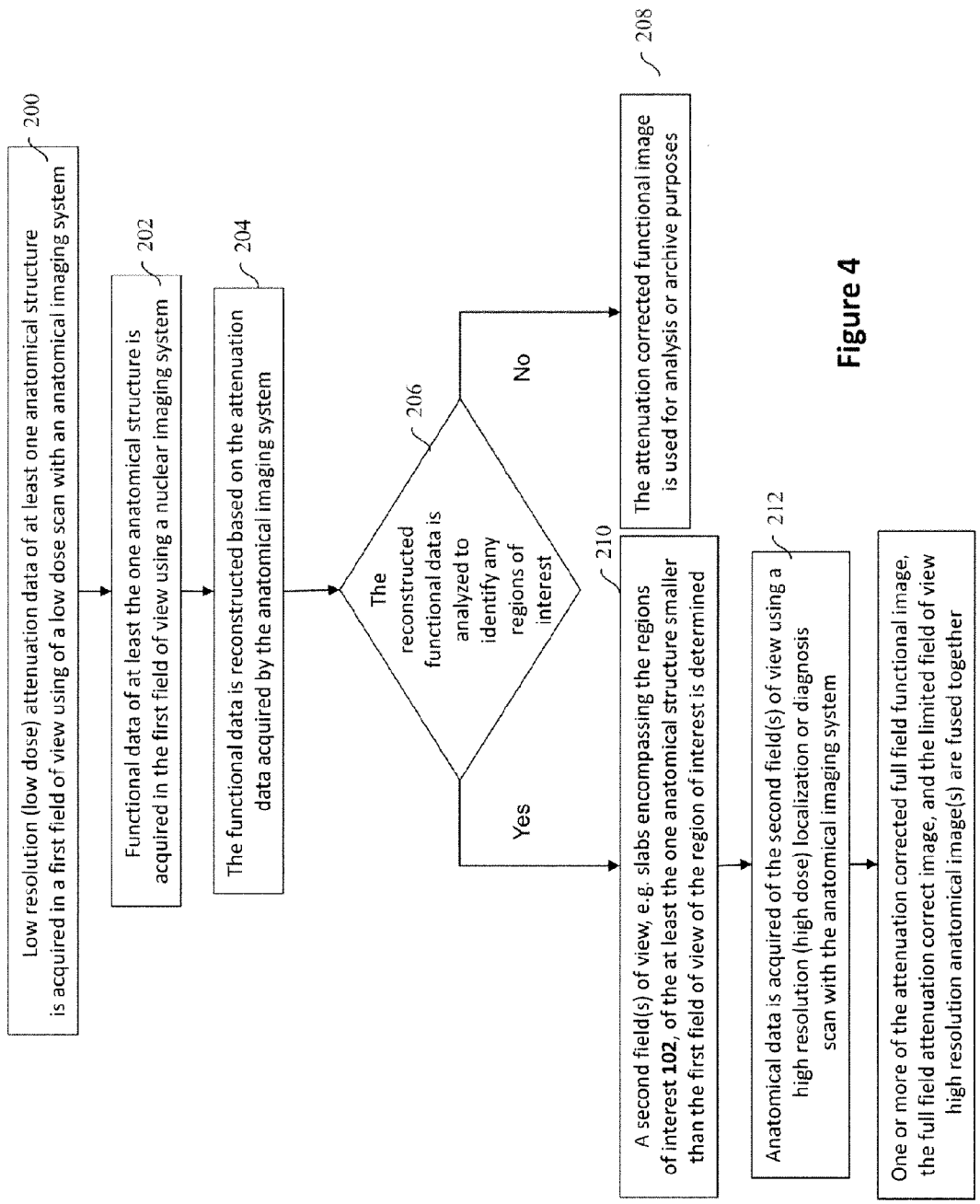
FIG. 4 is a flowchart illustrating a method of low dose, high resolution diagnostic scanning.

With reference to FIG. 4, in a step 200, low resolution (low dose) attenuation data of at least one anatomical structure is acquired in a first field of view 108 using of a low dose scan with an anatomical imaging system. In a step 202, functional data of at least the one anatomical structure is acquired in the first field of view 106 using a nuclear imaging system. In a step 204, the functional data is reconstructed based on the attenuation data acquired by the anatomical imaging system. In a step 206, the reconstructed functional data is analyzed to identify any regions of interest 102. If it is determined that detailed anatomical data is not beneficial for diagnosis, the attenuation corrected functional image is used for analysis or archive purposes in a step 208. If it is determined that detailed anatomical data is beneficial for diagnosis, a second field(s) of view 110, e.g. slabs encompassing the regions of interest 102, of the at least one anatomical structure smaller than the first field of view of the region of interest is determined in a step 210. In a step 212, anatomical data is acquired of the second field(s) of view using a high resolution (high dose) localization or diagnosis scan with the anatomical imaging system. In a step 214, one or more of the attenuation corrected full field functional image, the full field attenuation correct image, and the limited field of view high resolution anatomical image(s) are fused together to generate a full field image which depicts high resolution anatomical information covering the regions of interest 102 and low resolution anatomical information over the rest of the first field of view.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A hybrid imaging system comprising:
   a first imaging system configured to acquire low resolution anatomical data of a first field of view of an anatomical structure;
   a second imaging system configured to acquire functional data of the first field of view of the anatomical structure;
   one or more processors configured to reconstruct the functional data based on attenuation data from the acquired low resolution anatomical data into an attenuation corrected functional image;
   in response to the attenuation corrected image showing regions of interest, with the first imaging system or another imaging system acquiring high resolution anatomical data of one or more portions of the first field of view containing the regions of interest; and
   with the one or more processors, reconstructing the high resolution anatomical data into one or more high resolution anatomical images of the regions of interest.

2. The hybrid imaging system according to claim 1, wherein the low resolution anatomical data is acquired in the first field of view and the high resolution anatomical data is acquired in one or more second field(s) of view, each second field of view being smaller than the first field of view.

3. The hybrid imaging system according to claim 1, wherein the first imaging system includes a CT imaging system and the second imaging system includes a PET imaging system.

4. The hybrid imaging system according to claim 1, wherein the one or more processors are further configured to:
   analyze the attenuation corrected functional image to identify the regions of interest.

5. The hybrid imaging system according to claim 1, wherein the high resolution anatomical data is acquired with a CT scanner with a high radiation dose and the low resolution data is acquired with a radiation dose that is at least 85% lower than the high radiation dose.

6. The hybrid imaging system according to claim 1, wherein the one or more processors are further configured to:
   fuse the attenuation corrected functional image and the one or more high resolution anatomical image(s) together to generate a fused image.

7. The hybrid imaging system according to claim 1, wherein the one or more processors are further configured to:
   fuse the attenuation corrected functional image, the low resolution anatomical image, and the high resolution anatomical image to generate a fused image including functional information covering the first field of view, high resolution anatomical information covering the regions of interest, and low resolution anatomical information over the rest of the first field of view.

8. A method comprising:
   acquiring low resolution anatomical data of a first field of view of an anatomical structure;
   acquiring functional data of the first field of view of the anatomical structure;
   reconstructing the functional data using the low resolution anatomical data for attenuation correction into an attenuation corrected functional image; and
   analyzing the attenuation corrected functional image to identify any regions of interest;

acquiring high resolution anatomical data in second fields of view which encompass the regions of interest, the second fields of view being smaller than and confined in the first field of view; and reconstructing the high resolution anatomical data into one or more high resolution images.

9. The method according to claim 8, further including:

in response to identifying no regions of interest, not acquiring high resolution anatomical data.

10. The method according to claim 8, further including:

reconstructing the low resolution anatomical data into a low resolution anatomical image.

11. The method according to claim 10, further including:

fusing the attenuation corrected functional image, the low resolution anatomical image, and the one or more high resolution anatomical image(s) together to generate a fused image.

12. The method according to claim 8, wherein the low resolution and high resolution data are acquired with a CT scanner and the functional data is acquired with a PET scanner.

13. The method according to claim 8, wherein the low resolution anatomical data is acquired with a dose that is at least 85% lower than the radiation dose used to acquire the high resolution anatomical data.

14. A non-transitory computer readable medium carrying a computer program which controls a processor to perform the method of claim 8.

15. An imaging system comprising:

an anatomical scanner which generates anatomical data;

a functional scanner which generates functional data;

one or more processors programmed to perform the method according to claim 11; and a display configured to display the fused image.

16. A method comprising:

generating a functional image covering a first field of view of a patient;

analyzing the functional image for regions of interest including:

in response to identifying one or more regions of interest in the functional image, generating one or more high resolution anatomical images covering one or more second fields of views, each second field of view encompassing at least one region of interest and being smaller than and contained in the first field of view, and in response to identifying no regions of interest, terminating the method without generating a high resolution anatomical image.

17. The method according to claim 16, further including:

generating a low resolution anatomical image covering the first field of view;

using the low resolution anatomical image to correct the functional image for radiation attenuation.

18. The method according to claim 17, further including:

combining functional image, the one or more high resolution anatomical images, and the low resolution anatomical image to generate a fused image.

19. The method according to claim 16, further including:

using a PET imaging system to acquire functional image data; and reconstructing the functional data into the functional image.

20. The method according to claim 16, further including:

using a CT imaging system to acquire high resolution anatomical image data; and reconstructing the high resolution image data into the high resolution anatomical images.

* * * * *